US006847841B1

(12) United States Patent
El Hatw

(10) Patent No.: US 6,847,841 B1
(45) Date of Patent: Jan. 25, 2005

(54) DETECTOR OF LIVING TISSUE STRENGTH AND ELECTRICAL RESISTANCE AND ACTIVITY

(75) Inventor: Mohamed Khaled-Mohamed El Hatw, Cairo (EG)

(73) Assignee: Mohamed Khaled Mohamed El Hatw, Nasr (EG)

( * ) Notice: Subject to any disclaimer, the term of this patent is extended or adjusted under 35 U.S.C. 154(b) by 328 days.

(21) Appl. No.: 09/721,610

(22) Filed: Nov. 24, 2000

(30) Foreign Application Priority Data

Nov. 22, 1999 (EG) .......................................... 1999111492

(51) Int. Cl.$^7$ ................................................ A61B 5/05

(52) U.S. Cl. ..................................................... 600/547

(58) Field of Search .......................... 608/547; 600/372, 600/382, 384, 386, 461, 476, 477, 478, 300, 550, 562, 373, 424; 433/27, 32, 72; 606/130, 170, 159, 205

(56) References Cited

U.S. PATENT DOCUMENTS

| 4,184,486 A | * | 1/1980 | Papa ........................... 600/373 |
| 5,626,597 A | * | 5/1997 | Urban et al. ................. 606/170 |
| 5,810,742 A | * | 9/1998 | Pearlman ..................... 600/547 |
| 6,337,994 B1 | * | 1/2002 | Stoianovici et al. ......... 600/547 |

* cited by examiner

Primary Examiner—Max F. Hindenburg
Assistant Examiner—Brian Szmal

(57) ABSTRACT

A diagnostic cylindrical probe introduced through the body surfaces to the target tissue to detect the resistance of the tissues to piercing, its electrical activity and its resistance to passage of electrical current to identify the nature of the tissue and predict the nature of its pathology during needle biopsy has a sharp piercing tip attached to its end through a coiled wire to slide over the surface of an inbuilt changeable electrical resistance incorporated in an electrical circuit to detect the mechanical resistance of the tissues to piercing, a sensor at its tip incorporated in a second electrical circuit to detect the electrical impedance of the target tissue and a secondary electrically isolated sensor incorporated with the first sensor in a third electrical circuit to detect the electrical resistance of the tissues to passage of electrical current.

3 Claims, 3 Drawing Sheets

DETECTOR OF LIVING TISSUE STRENGTH AND ELECTRICAL RESISTANCE AND ACTIVITY

BACKGROUND OF THE INVENTION

1. The Old Art

Tissue biopsy is essential for many studies including histopathological, Immunohistological & histochemical studies.

Biopsy can be done by a biopsy needle with a sharp edge to cut the sample & carry it out side the body. In the needle biopsy metal sheath passes an internal metal needle to allow piercing of the overlying tissues.

2. Defect in the Old Art

There is no sure sign that the tip of the needle has arrived to the target tissue this depends partially on the accuracy of the imaging technique & the experience of the operator, there is also a delay in the diagnostic results.

It is not uncommon that valuable days are lost to receive a pathological report of failure to take the biopsy from the target tissue.

BRIEF SUMMARY OF THE INVENTION

This apparatus is used during needle biopsy where it is introduced in the needle biopsy sheath instead of the needle to observe measure or record the resistances of the tissues to piercing, its resistance to passage of electrical current. It also records the electrical activity of the tissue (if any). These three functions together can help in identification of the nature of the tissue during needle biopsy before the actual cutting of the tissue as well as prediction of the nature of its pathology.

Figure 1:
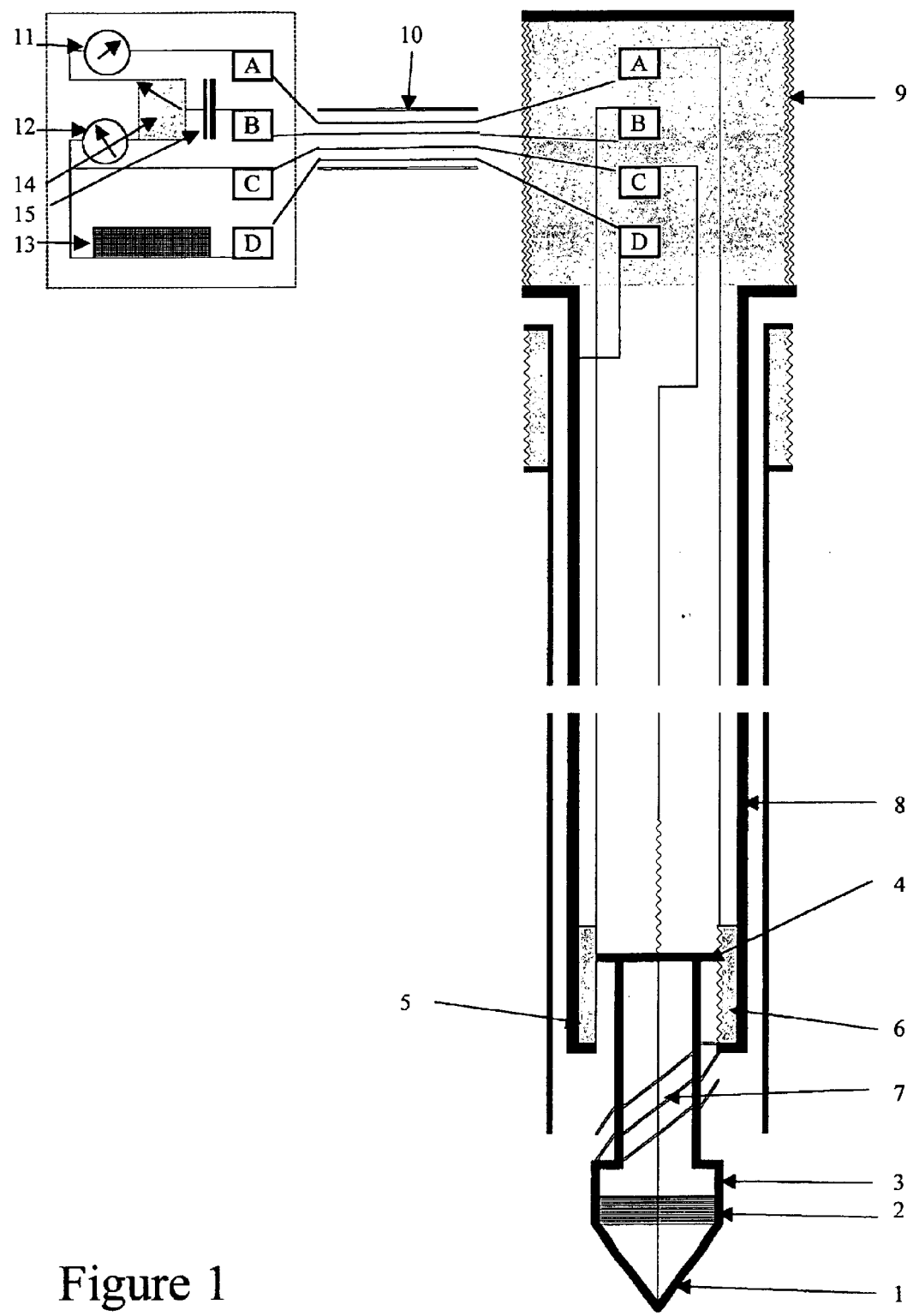
FIG. 1 The sensor: The tip of the sensor (1) An electrical isolator (2) The base of the tip of the sensor (3) two side wings (4) metal blade (5) electrical resistance (6) A spiral coil (7) The body of the sensor (8) The base of the sensor (9) The cable: (10) The monitor: Outlet (B) on the base of the monitor (9) The monitor auditory, visual electrical registering unit (11). The monitor auditory, visual, electrical registering unit (12). The monitor registering unit (13). The electrical switch (14). A suitable electric source (15)

3b: a diagrammatic presentation of the electrical resistance showing higher resistance in peinephric fat (4).

3c: a diagrammatic presentation of the electrical activity showing higher activity in the muscles (3). Electrical activity of the renal cortex (6) which is variable in different glomerular diseases is also expected.

DETAILED DESCRIPTION OF THE INVENTION

1—Theoretical Background

The living tissues differ in its consistency, type & density of its cells, connecting tissues & vascular supply, this variation makes tissues differ in their resistance to passage of a foreign body & resistance to passage of the electrical current. Some of the tissues as the heart and the brain have an evident electrical activity that can be detected from the surface of the skin. Other tissues have less evident electrical activity that can not be detected unless the detector reaches the target tissue.

The idea os this apparatus depends on studying these three characters during taking the biopsy. This will help to ensure arrival of the needle to the target tissue & predict any pathological changes.

2—The Structure of the Apparatus

A—The Sensor

The shape, the length & the diameter of the sensor is identical to the internal needle of the renal biopsy needle. This similarity allows its replacement after doing the target function.

The lip of the sensor (1) is pointed and connected to the terminal (C) by an isolated wire that passes in the sensor.

An electrical isolator (2) that isolates the tip of the sensor (1) from the base of the tip of the sensor (3).

The base of the tip of the sensor (3) is metal & is able to move vertically together with the tip of the sensor (1) & the electrical isolator (2). It has two side wings (4).

The first wing touches a metal blade (5) which is attached to the terminal (B).

The second wing touches a the coil of an electrical resistance (6) which is attached to the terminal (A).

A spiral coil (7) It is from a non conducting material & it separates the body the sensor (8) from the base of the tip of the sensor (3).

The body of the sensor (8) is a metal tube attached to the terminal (D) & is isolated from its internal contents (The electrical resistance (10), the metal blade (5) & the base of the tip of the sensor (3)).

The base of the sensor (9) it is formed from a non conducting material similar to the base of the original internal biopsy needle. To it the electrical terminals (A,B,C,D) are attached.

B—The Cable

A cable (10) with four isolated wires attach the four terminals of the monitor to the corresponding terminals on the base of the sensor.

C—The Monitor

A visual, auditory or electrical intensity or voltage detector (Ammeter or voltmeter) with possibility of adding a registering unit on sensitive paper to monitor & record the physical resistance to entry of the sensor in different tissues while applying a constant pressure.

A visual, auditory or electrical intensity or voltage detector (Ammeter or voltmeter) with possibility of adding a registering unit on sensitive paper to monitor & record the electrical resistance to passage of the electrical current in different tissues The registering unit for the electrical activity of different tissues is similar to that used in the ElectroCardioGagraph (E.C.G.), the Electro EncephaloGraph (E.E.G.) or the ElectroMyoGagraph (E.M.G.). The prementioned devices magnify the intrinsic electrical activity of the tissues & change it into movements of a hot needle over a heat sensitive paper or alternatively express it on the screen.

D—The Electrical Circuits

1—A Circuit to Study the Physical Resistance

Outlet (A) on the base of the sensor (9).

The connecting wire in the cable (10).

Outlet (A') on the monitor.

The monitor auditory, visual, electrical registering unit (11).

The electrical switch (14).

A suitable electric source (15) that can be tolerated by the body (e.g. not more than 12 Volts)

Outlet (B) on the monitor.

The connecting wire in the cable (10).

Outlet (B) on the base of the sensor (9).

A wire passing through the body of the sensor (8) connecting the outlet (B) to the metal blade (5).

The metal blade (5).

The base of the tip of the sensor (3).

The electrical resistance (6).

A wire connecting the electrical resistance (6) to the outlet (A) on the base of the sensor (9).

With increasing physical resistance to the passage of the sensor the tip of the sensor (1), the electrical isolator (2) & the base of the tip of the sensor (3) move vertically together to decrease the electrical resistance. This electrical changes can be detected by the monitor.

2—A Circuit to Study the Electrical Resistance

Outlet (C) on the base of the sensor (9).

The connecting wire in the cable (10).

Outlet (C") on the monitor.

The monitor auditory, visual electrical registering unit (12).

The electrical switch (14).

A suitable electric source (15)

Outlet (B') on the monitor.

The connecting wire in the cable (10).

Outlet (B) on the base of the sensor (9).

A wire passing through the body of the sensor (8) connecting the outlet (B) to the metal blade (5).

The metal blade (5).

The base of the tip of the sensor (3).

The living tissue around the tip of the sensor (1)

A wire connecting the tip of the sensor (1) to the outlet (C) on the base of the sensor (9).

The electrical resistance to passage of the electrical current differ in the living tissue according to its type & the pathological changes that can be detected by the monitor.

3—A Circuit to Study the Electrical Activity

Outlet (C) on the base of the sensor (9).

The connecting wire in the cable (10).

Outlet (C) on the monitor.

The monitor registering unit (13).

Outlet (D') on the monitor.

The connecting wire in the cable (10).

Outlet (D) on the base of the sensor (9).

A wire passing through the body of the sensor (8) connecting the outlet (D) to the metal body of the sensor (8).

The metal sheath of the biopsy needle (14) which is touching the metal body of the sensor. [but it is not considered as part of the sensor].

Different living tissues through which the biopsy needle passes & works as the earth terminal to the registering unit (13).

The target living tissue for measuring the electrical activity which is in direct contact with the tip of the sensor (1)

The tip of the sensor (1)

A wire connecting the tip of the sensor (1) to the outlet (C) on the base of the sensor (9).

The outlet (C) on the base of the sensor (9).

E—Computerized Analysis Unit

After completing the data derived from studying different types of normal & pathological tissues, a computer program can be designed to keep these data.

During tissue biopsy data about the anatomical position of the biopsy can be inserted & the computer program will compare the stored data with the patient's data to give instantaneous diagnosis of the anatomical & pathological data of the tissue at the tip of the sensor.

3—How to Use the Apparatus?

1—The patient is prepared for renal biopsy as usual (positioning sterilization, anesthesia & localization of the target tissue or organ by the proper means of imaging).

2—Replace the inner needle with a suitable sensor with identical shape & size.

3—Switch on the electric switch (14) & apply a constant pressure to push the biopsy needle with the sensor inside in the direction of the target tissue. Observe the monitor reading about the physical & electrical resistance of the tissues while pushing the biopsy needle.

4—To verify the nature of the target tissue or the tissue in the way of the needle, switch off the electric switch (14) & record the intrinsic activity of the tissue surrounding the tip of the sensor (1).

5—To cut the target tissue by the Uro-cut biopsy needle model replace the sensor with the original grooved needle, move the sheath up to expose the groove the down to cut the tissue with the sharp metal sheath then withdraw the biopsy needle out with the needle & the tissue inside as usual.

6—To cut the target tissue by the Mangini biopsy needle remove the sensor, apply a suction syringe & move the sheath up & down to cut the target tissue.

An Expected Example During Renal Biopsy

Figure 2:
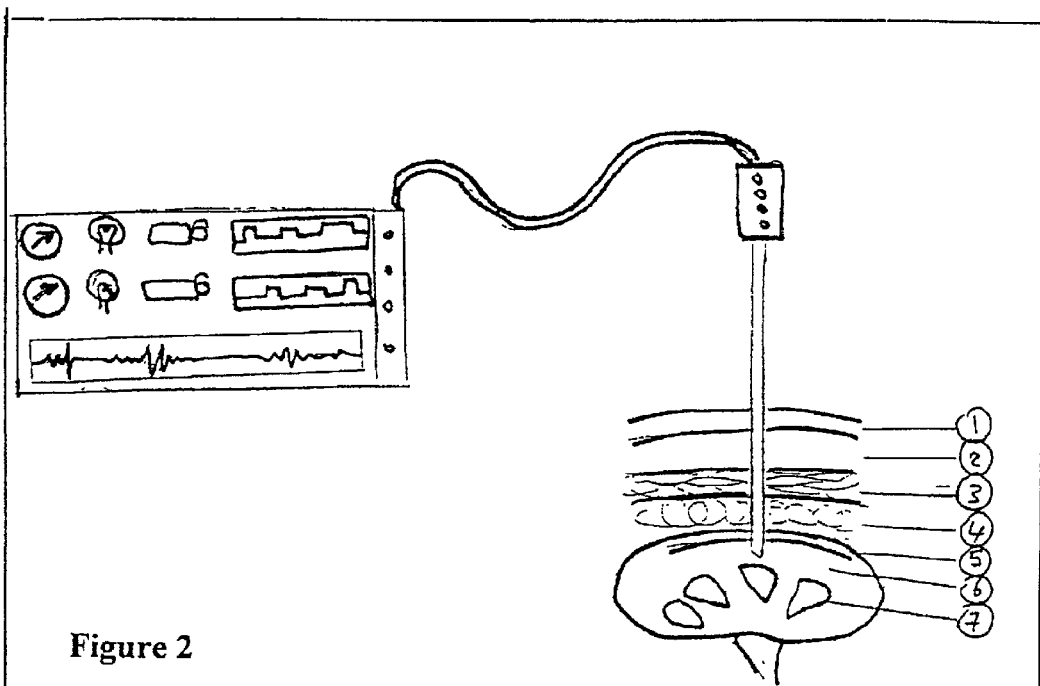
FIG. 2: the sensor with the sheath passing through the skin (1), the subcutaneous tissue (2), the muscles (3), the peinephric fat (4) The renal capsule (5) the renal cortex (6) & the renal medulla (7).

1—FIG. 2: The sensor with the sheath passing through the skin (1), the subcutaneous tissue (2), the muscles (3), the peinephric fat (4) The renal capsule (5) the renal cortex (6) & the renal medulla (7).

Figure 3:
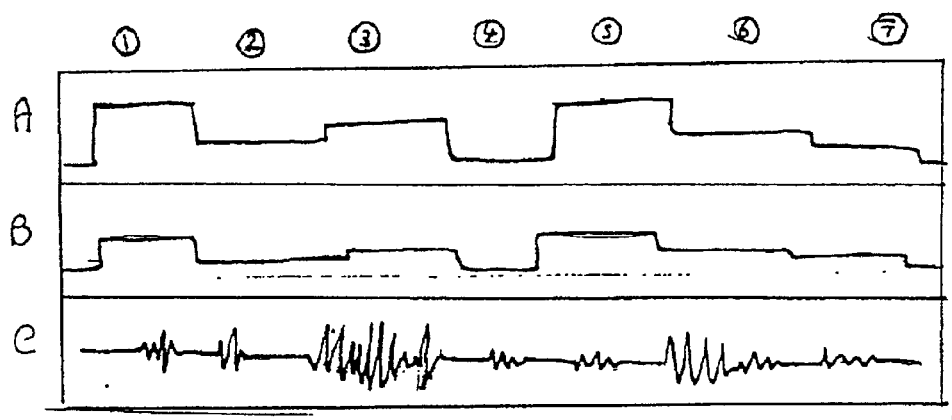
FIG. 3a: a diagrammatic presentation of the physical resistance showing higher resistance in the skin (1) & the renal capsule (2).
Figure 4:
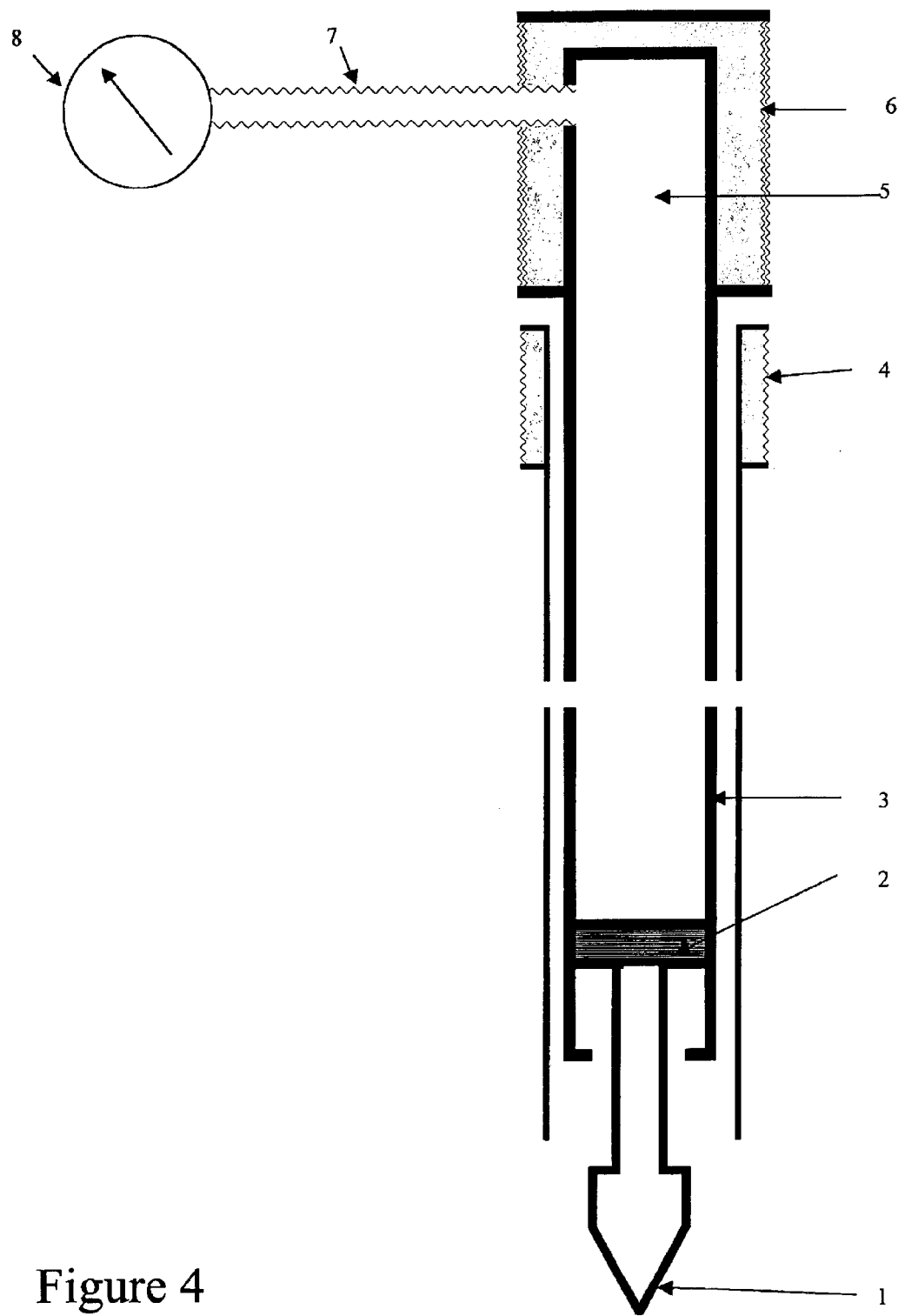

2—FIG. 3a: A diagrammatic presentation of the physical resistance record showing higher resistance in the skin (1) & the renal capsule (2).

FIG. 3b: A diagrammatic presentation of the electrical resistance record showing higher resistance in perinephric fat (4).

FIG. 3c: A diagrammatic presentation of the electrical activity showing higher activity in the muscles (3). Electrical activity of the renal cortex (6) which is variable in different glomerular diseases is also expected.

4—How to Get Use of the Detector?

A—Complete the Relevant Studies

Studies of living tissues & living animals can verify the characters of healthy living tissues.

Noting that the apparatus can work through the biopsy needle no non predetermined human invasive studies will be required Comparison of the detector findings with data derived from different imaging techniques during biopsy & the results of pathological studies & with the growing data of the electrical disturbances of different disorders (e.g. loss of the glomerular negative charges in Nephrotic Syndrome & recently the electrical disturbances in some hepatic disorders) will help to verify the significance of the detector & feed its computerized analysis units.

B—Manufacture

Supply the sensor as a disposable sterile single use product.

The cable & the monitor can be manufactured as permanent devices. Alternatively a small electric lamb or ring can be added to the base of the sensor to be used for detection of physical & electrical resistance.

C-Utilization

The sensors will be consumed with the rate of biopsies taken.

The monitors cables & data analysis units will be consumed with a number parallel to the number of the medical units performing biopsy.

What I claim as my invention is:

1. A diagnostic cylindrical probe introduced through the body to detect the mechanical resistance of the tissue to piercing, comprising a cylindrical probe body a compressible pointed piercing tip having a base mounted at a distal end of the cylindrical probe body through a coiled wire sliding over the surface of an inbuilt changeable electrical resistance and over a metal blade, a first wire connecting the metal blade to an electrical source, the first wire passing through the body of the probe;

a second wire connecting the electrical resistance to the electrical source, the second wire passing through the body of the probe;

wherein the electrical source is located outside the probe; and a monitor comprising an Ammeter or Voltmeter to detect the electrical current intensity or voltage with the ability to add a registering unit using sensitive paper to monitor and record the electrical resistance, wherein the nature of the target tissue is detected by changing the mechanical resistance faced by the tip of the probe during its passage in the target tissues into a change in the electrical resistance.

2. A diagnostic cylindrical probe introduced through the body to detect the electrical resistance of the target tissue comprising a pointed piercing tip including two electrically isolated electrodes connected to an electrical circuit to detect the electrical resistance of the tissue to passage of an electrical current;

a first wire running inside the body of the probe with one of its terminals at the tip of the probe and the other terminal connected to an electrical source;

the electrical source is located outside the probe;

an Ammeter or Voltmeter to detect the electrical current intensity or voltage with possibility of adding a registering unit on sensitive paper and a second wire running inside the body of the probe with one end connected to the electrical source & and the other end is located at the tip of the probe near the end of the said first wire, wherein the nature of the target tissue is detected by monitoring the electrical resistance exerted by the tissue surrounding the tip.

3. A diagnostic cylindrical probe introduced through the bode to detect the electrical activity of target tissue, comprising an electrical circuit to detect the electrical activity;

a pointed piercing tip electrically isolated from the probe by a transverse insulator to detect the electrical activity of the target tissue;

a first wire running inside the body of the probe with one of its terminals at the tip of the probe and the other terminal connected to an electrical activity monitor; and a second wire connecting the electrical activity monitor to the body of the probe, which operates as a neutral isoelectric point;

wherein the nature of the target tissue is detected by monitoring the electrical activity of the tissue surrounding the tip.

* * * * *